United States Patent [19]

Endo et al.

[11] Patent Number: 5,707,836

[45] Date of Patent: Jan. 13, 1998

[54] PRODUCTION OF ALKYLENE OR PHENYLENEDIAMINE DISUCCINIC ACID FROM FUMARIC ACID AND A DIAMINE USING LYASE FROM MICROBES

[75] Inventors: Takakazu Endo; Yoshihiro Hashimoto; Rikiya Takahashi, all of Kanagawa, Japan

[73] Assignee: Nitto Chemical Industry Co., Ltd., Tokyo, Japan

[21] Appl. No.: 612,437

[22] Filed: Mar. 7, 1996

[30] Foreign Application Priority Data

| Mar. 10, 1995 | [JP] | Japan | 7-078390 |
| Mar. 24, 1995 | [JP] | Japan | 7-090101 |
| Apr. 27, 1995 | [JP] | Japan | 7-125680 |
| Jun. 14, 1995 | [JP] | Japan | 7-170476 |
| Jul. 7, 1995 | [JP] | Japan | 7-194042 |
| Sep. 22, 1995 | [JP] | Japan | 7-268029 |

[51] Int. Cl.$^6$ .................................. C12P 13/20
[52] U.S. Cl. .................................. 435/109; 435/232
[58] Field of Search .................. 435/109, 232, 435/830, 874

[56] References Cited

U.S. PATENT DOCUMENTS

| 3,158,635 | 11/1964 | Kezerian et al. | 260/429 |
| 3,198,712 | 8/1965 | Takahashi et al. | 435/109 |
| 3,943,038 | 3/1976 | Morinaga et al. | 435/109 |

FOREIGN PATENT DOCUMENTS 60-168395  8/1985  Japan.

OTHER PUBLICATIONS

Neal JA et al., "Stereospecific Ligands and Thier Complexes. I. A Cobalt (III) Complex of Ethylenediaminedisuccinic Acid" vol. 7, No. 11, Nov. 1968.

Nishikiori T. et al., J. Antibiotics XXXVII (4):426–7 (1984).

*Primary Examiner*—Sandra E. Saucier
*Attorney, Agent, or Firm*—Sughrue, Mion, Zinn, Macpeak & Seas, PLLC

[57] ABSTRACT

A method of producing an optically active amino acid is disclosed which comprises converting a mixture of an amino group-containing compound, e.g., an alkanediamine, and fumaric acid into an optically active amino acid by the action of a microorganism. The method is useful in industrially producing an optically active amino acid from the inexpensive starting materials, i.e., fumaric acid and an amino compound, under mild conditions of ordinary temperature and ordinary pressure.

12 Claims, No Drawings

PRODUCTION OF ALKYLENE OR PHENYLENEDIAMINE DISUCCINIC ACID FROM FUMARIC ACID AND A DIAMINE USING LYASE FROM MICROBES

FIELD OF THE INVENTION

The present invention relates to a method of producing an optically active amino acid from fumaric acid and an amino group-containing compound by the action of a microorganism. Besides being important as an intermediate for medicines or agricultural chemicals, optically active amino acids are expected to be useful in applications such as chelating agents and detergent builders because of their specific property of catching heavy metals and properties attributable to optical activity, such as susceptibility to biodegradation.

BACKGROUND OF THE INVENTION

A mixture of optical isomers of an amino acid represented by formula (I) described below can be easily synthesized by a technique of organic synthesis from various amines and maleic or fumaric acid. However, in the case of synthesizing optically active amino acids by organic synthesis, use of optically active aspartic acid or the like as a starting material is necessary. For example, it has been reported that a mixture of optical isomers of diaminoalkylene-N,N'-disuccinic acid, a compound having two asymmetric carbon atoms, can be produced by a technique of organic synthesis from maleic acid and various diamines (see U.S. Pat. No. 3,158,635), and that an optically active isomer thereof can be synthesized by a technique of organic synthesis from L-aspartic acid and dibromoethane (see John A. Neal et al., *Inorganic Chem.*, 7, 2405 (1968)). It is, however, difficult to produce such optically active isomers at low cost to provide these compounds suitable for general use.

S,S-ethylenediamine-N,N'-disuccinic acid is a diaminoalkylene-N,N'-disuccinic acid produced by a microorganism. This acid, serving as a specific inhibitor for phospholipase C, was isolated from a culture of ray fungus MG417-CF17 strain and identified (see T. Nishikiori et al., *J. Antibiotics*, 37, 426 (1984)). However, this method using the ray fungus has extremely low production efficiency and is unsuitable for industrial production.

SUMMARY OF THE INVENTION

As a result of extensive investigation to produce an optically active amino acid represented by formula (I), the present inventors have found that optically active amino acids, in particular S,S-diaminoalkylene-N,N'-disuccinic acids and R,S-diaminoalkylene-N,N'-disuccinic acids, can be efficiently produced from inexpensive starting materials, i.e., fumaric acid and amino group-containing compounds, by utilizing the catalytic action of a microorganism. The present invention has been achieved based on this finding.

That is, the present invention provides a method of producing an optically active amino acid represented by formula (I):

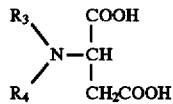

which comprises treating a mixture of an amino group-containing compound represented by formula (II) and fumaric acid with a microorganism having a lyase activity, which may have been treated,

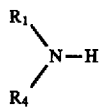

wherein $R_1$ and $R_2$ may be the same or different and each represents a hydrogen atom (provided that $R_1$ and $R_2$ are not simultaneously a hydrogen atom), an amino-substituted or carboxy-substituted alkyl (preferably $C_1$ to $C_4$) group, an amino-substituted cycloalkyl (preferably $C_3$ to $C_6$) group or an amino-substituted aryl group; and $R_3$ and $R_4$ are the same with $R_1$ and $R_2$ or each represents a group having a structure linked at least one amino group of $R_1$ and $R_2$ with succinic acid.

The preferred compound of the optically active amino acid represented by formula (I) is a compound represented by formula (III):

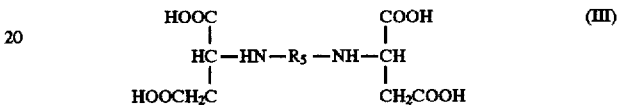

wherein $R_5$ represents an alkylene group, a cycloalkylene group or a phenylene group, preferably an alkylene group.

In the amino group-containing compound represented by formula (II), it is preferred that at least one of $R_1$ and $R_2$ is an amino-substituted alkyl group, an amino-substituted cycloalkyl group or an amino-substituted aryl group and the more preferred compound thereof is a compound represented by formula (IV):

wherein $R_5$ represents an alkylene group, a cycloalkylene group or a phenylene group, preferably an alkylene group.

Although the mechanism of reaction in the method of the present invention has not been elucidated so far, the reaction is thought to proceed by a mechanism similar to that of reactions catalyzed by aspartate ammonia-lyase, arginosuccinate ammonia-lyase or the like, which are generally present in microorganism cells.

DETAILED DESCRIPTION OF THE INVENTION

Examples of the amino group-containing compound (hereinafter, referred to as an amino group) represented by the formula (II) include monoamines such as glycine, iminodiacetic acid, 3-aminopropionic acid, and 3,3'-iminodipropionic acid, alkane- or cycloalkanediamines having 1 to 6 carbon atoms such as ethylenediamine, propanediamine, butanediamine, pentanediamine, hexanediamine and cyclohexanediamine, phenylenediamines such as 1,3-phenylenediamine and 1,4-phenylenediamine, and polyamines such as triethylenetetramine, tetraethylenepentamine, and pentaethylenehexamine.

Representative optically active amino acids represented by the formula (I) which may be obtained by the present invention include S,S- or R,S-isomers of diaminoalkylene-, phenylenediamine- or diaminocycloalkane-N,N'-disuccinic acids such as ethylenediamine-N,N'-disuccinic acid, 1,3-propanediamine-N,N'-disuccinic acid, 2-methyl-1,3-propanediamine-N,N'-disuccinic acid, 1,2-cyclohexanediamine-N,N'-disuccinic acid, 1,3-cyclohexanediamine-N,N'-disuccinic acid and 1,4-cyclohexanediamine-N,N'-disuccinic acid, 1,3-phenylenediaminedisuccinic acid, 1,4-phenylenediaminedisuccinic acid, and S- or R-isomers of aspartic acid-N-monoacetic acid, aspartic acid-N,N-diacetic acid, aspartic acid-N-monopropionic acid, aspartic acid-N-2-propionic acid and aspartic acid-N-2-glutaric acid.

The microorganisms for use in the present invention include, for example, a microorganism belonging to any of the genera Burkholderia, Arthrobacter, Paracoccus, Hafnia, Acidovorax, Sphingomonas, Brevundimonas, Pseudomonas and Escherichia. Specific examples thereof include *Burkholderia sp.* KK-5 (FERM BP-5412), *Burkholderia sp.* KK-9 (FERM BP-5413), *Arthrobacter sp.* KK-3 (FERM BP-5414), *Paracoccus sp.* KK-6 (FERM BP-5415), *Hafnia alvei* ATCC 9760, *Acidovorax sp.* TN-51 (FERM BP-5416), *Sphingomonas sp.* TN-28 (FERM BP-5419), *Brevundimonas sp.* TN-30 (FERM BP-5417), *Pseudomonas sp.* TN-131 (FERM BP-5418), and *Escherichia coli* JM 109 (ATCC 53323). Of these microorganisms, the strains ATCC 9760 and ATCC 53323 are known and easily available from the American Type Culture Collection (ATCC). The other microorganisms were newly isolated from soils by the present inventors, and have been deposited with National Institute of Bioscience and Human Technology, Agency of Industrial Science and Technology, Ministry of International Trade and Industry, No. 1–3, Higasgi 1-chome, Tsukuba-shi, Ibaraki-ken, 305, Japan under the respective accession numbers shown above. Bacteriological properties thereof are as shown below.

| Bacteriological Properties: | Strain KK-5 | Strain KK-9 |
|---|---|---|
| Morphology | bacilliform | bacilliform |
| Gram staining | – | – |
| Spore | – | – |
| Mobility | + | + |
| Flagella | several polar flagella | several polar flagella |
| Require for free oxygen | aerobic | aerobic |
| Oxidase | + | + |
| Catalase | + | + |
| OF test | O | O |
| Formation of fluorescent pigment | – | – |
| Quinone system | Q-8 | Q-8 |
| Reduction of nitrate | – | + |
| Indole formation | – | – |
| Fermentation of glucose | – | – |
| Arginine dihydrolase | – | – |
| Urea decomposition | – | – |
| Esculin decomposition | – | – |
| Gelatin liquefaction | – | – |
| PNPG | + | – |
| Acid formation from xylose | + | + |
| Utilization | | |
| Glucose | + | + |
| L-Arabinose | + | + |
| D-Mannose | + | + |
| D-Mannitol | + | + |
| Maltose | – | – |
| Potassium gluconate | + | + |
| n-Capric acid | + | + |
| Adipic acid | – | – |
| dl-Malic acid | + | + |
| Citric acid | + | – |
| Phenyl acetate | + | + |

| Strain KK-3 | |
|---|---|
| Morphology | polymorphic bacilliform |
| Gram staining | + |
| Spore | – |
| Mobility | – |

| Bacteriological Properties: | |
|---|---|
| Require for free oxygen | aerobic |
| Oxidase | – |
| Catalase | + |
| Color of colony | no characteristic color |
| Acid fastness | – |
| Rod-coccus cycle | + |
| Elongation around colony | none |
| Diamino acid of cell walls | lysine |
| Glycolyl test | – (acetyl type) |
| Arabinogalactan polymer of cell walls | – (estimated from acid hydrolyzate of all cells) |
| Quinone system | MK-9(H$_2$), 8(H$_2$) |
| GC content of DNA (mol %) | 65 (HPLC method) |

| Strain KK-6 | |
|---|---|
| Morphology | coccoid or short bacilliform |
| Gram staining | – |
| Spore | – |
| Mobility | – |
| Require for free oxygen | aerobic |
| Oxidase | + |
| Catalase | + |
| OF test | – |
| Color of colony | no characteristic color |
| Accumulation of PHB | + |
| Denitrification | – |
| Reduction of nitrate | + |
| Reduction of nitrite | – |
| Quinone system | Q-10 |
| GC content of DNA (mol %) | 64 (HPLC method) |

| Strain TN-51 | |
|---|---|
| Morphology | bacilliform |
| Gram staining | – |
| Spore | – |
| Mobility | + |
| Flagella | single polar flagella |
| Require for free oxygen | aerobic |
| Oxidase | + |
| Catalase | + |
| OF test | O |
| Color of colony | no characteristic color |
| Accumulation of PHB | + |
| Growth at 40° C. | – |
| Cleavage of protocatechuate | meta form |
| Carotenoid pigment | – |
| Assimilation of glucose | + |
| Ability to utilize hydrogen | – |
| Quinone system | Q-8 |

| Strain TN-28 | |
|---|---|
| Morphology | bacilliform |
| Gram staining | – |
| Spore | – |
| Mobility | + |
| Flagella | single polar flagella |
| Require for free oxygen | aerobic |
| Oxidase | + |
| Catalase | + |
| OF test | – |
| Color of colony | yellow |
| Formation of fluorescent pigment | – |
| Quinone system | Q-10 |
| Reduction of nitrate | – |
| Indole formation | – |
| Fermentation of glucose | – |
| Arginine dihydrolase | – |
| Urea decomposition | – |
| Esculin decomposition | + |
| Gelatin liquefaction | – |
| PNPG | – |
| Utilization | |
| Glucose | + |

Bacteriological Properties:

| | |
|---|---|
| L-Arabinose | − |
| D-Mannose | + |
| D-Mannitol | − |
| N-Acetyl-D-glucosamine | + |
| Maltose | + |
| Potassium gluconate | − |
| n-Capric acid | − |
| Adipic acid | − |
| dl-Malic acid | + |
| Sodium citrate | − |
| Phenyl acetate | − |

Strain TN-30

| | |
|---|---|
| Morphology | bacilliform |
| Gram staining | − |
| Spore | − |
| Mobility | + |
| Flagella | single polar flagella |
| Require for free oxygen | aerobic |
| Oxidase | + |
| Catalase | + |
| OF test | − |
| Color of colony | no characteristic color |
| Formation of fluorescent pigment | − |
| Accumulation of PHB | + |
| Auxotrophy | positive |
| Quinone system | Q-10 |
| Reduction of nitrate | + |
| Indole formation | − |
| Fermentation of glucose | − |
| Arginine dihydrolase | − |
| Urea decomposition | − |
| Esculin decomposition | − |
| Gelatin liquefaction | − |
| PNPG | − |

Utilization

| | |
|---|---|
| Glucose | − |
| L-Arabinose | − |
| D-Mannose | − |
| D-Mannitol | − |
| N-Acetyl-D-glucosamine | − |
| Maltose | − |
| Potassium gluconate | + |
| n-Capric acid | − |
| Adipic acid | + |
| dl-Malic acid | − |
| Sodium citrate | + |
| Phenyl acetate | − |

Strain TN-131

| | |
|---|---|
| Morphology | bacilliform |
| Gram staining | − |
| Spore | − |
| Mobility | + |
| Flagella | single polar flagella |
| Require for free oxygen | aerobic |
| Oxidase | + |
| Catalase | + |
| OF test | − |
| Color of colony | yellow |
| Formation of fluorescent pigment | + |
| Quinone system | Q-9 |
| Reduction of nitrate | + |
| Indole formation | − |
| Fermentation of glucose | − |
| Arginine dihydrolase | − |
| Urea decomposition | − |
| Esculin decomposition | − |
| Gelatin liquefaction | − |
| PNPG | − |

Utilization

| | |
|---|---|
| Glucose | − |
| L-Arabinose | − |
| D-Mannose | − |

Bacteriological Properties:

| | |
|---|---|
| D-Mannitol | − |
| N-Acetyl-D-glucosamine | − |
| Maltose | − |
| Potassium gluconate | − |
| n-Capric acid | + |
| Adipic acid | − |
| dl-Malic acid | + |
| Sodium citrate | + |
| Phenyl acetate | − |

As a result of classification based on the foregoing bacteriological properties according to *Bergey's Manual of Systematic Bacteriology*, Vol. 1 (1984) and *Bergey's Manual of Determinative Bacteriology*, 9th ed. (1994), the strains KK-5 and KK-9 were each identified as a microorganism belonging to the genus Burkholderia, the strain TN-51 as a microorganism belonging to the genus Acidovorax, and the strain TN-131 as a microorganism belonging to the genus Pseudomonas. As a result of classification according to *Bergey's Manual of Systematic Bacteriology*, Vol. 2 (1986), the strain KK-3 was identified as a microorganism belonging to the genus Arthrobacter. As a result of classification according to *Bergey's Manual of Systematic Bacteriology*, Vol. 1 (1984), the strain KK-6 was identified as a microorganism belonging to the genus Paracoccus. As a result of classification according to *Bergey's Manual of Determinative Bacteriology*, 9th ed. (1994) and *Microbiol. Immunol.*, 34, 99 (1990), the strain TN-28 was identified as a microorganism belonging to the genus Sphingomonas. Further, as a result of classification according to *Bergey's Manual of Determinative Bacteriology*, 9th ed. (1994) and *Int. J. Syst. Bacteriol.*, 44, 499 (1994), the strain TN-30 was identified as a microorganism belonging to the genus Brevundimonas.

Embodiments of the present invention will be explained next.

Culture media for the microorganism used in the present invention are not particularly limited, and a synthetic or natural medium may be used as long as it appropriately contains an assimilable carbon source, nitrogen source and inorganic salt, a slight amount of an organic nutrient, etc. Addition of an amino acid such as ethylenediaminedisuccinic acid, ethylenediaminemonosuccinic acid, aspartic acid, glutamic acid, or histidine to the culture medium prior to culturing is preferred because this may produce cells having higher catalytic activity. Culturing conditions vary depending on the strain and culture medium used. In general, however, culturing may be aerobically conducted at a pH of the medium of from 4 to 10, preferably from 6 to 9, and a culturing temperature of from 20° to 45° C., preferably from 25° to 35° C., for 1 to 10 days until activity is maximized.

The reaction for producing the optically active amino acid represented by formula (I) is carried out by bringing either cells of any of the strains described above or a substance obtained by treating the same (e.g., dry cells, disrupted cells, a crude or purified enzyme, or immobilized cells or enzyme) into contact with a mixture of an amino compound represented by the formula (II) and fumaric acid in water or a buffer solution, e.g., a phosphoric acid buffer, carbonic acid buffer or boric acid buffer.

In general, the reaction is conducted at a temperature of from 0° to 50° C., preferably from 5° to 35° C., and a pH of from 5 to 11, preferably from 6 to 10. Although the concentrations of fumaric acid and the amino compound represented by formula (II) vary depending on the reaction temperature and pH used, they each may be in the range of from 0.1% to the saturation concentration. The amount of the microorganism or the like used is generally from 0.01 to 5.0% by weight of the amount of dry strain cells based on the amount of the substrates. The reaction may be conducted either batch-wise or continuously.

For isolating the amino acid from the reaction mixture after completion of the reaction, known techniques such as microorganism removal, concentration, and crystallization may be used.

The present invention will be explained below in more detail by reference to specific Examples. One of skill in the art will recognize the invention is not to be limited thereto. All the percentages are by weight unless otherwise indicated.

EXAMPLE 1

(1) Culture

Each of *Burkholderia sp.* KK-5 and *Burkholderia sp.* KK-9 was taken out from a slant medium in an amount of one platinum loop and inoculated into the following culture medium. These strains were cultured with shaking at 30° C. for 3 days.

| Composition of Culture Medium (pH 7, 100 ml) | |
|---|---|
| Glucose | 0.2 g |
| Yeast extract | 0.1 g |
| Polypeptone | 0.05 g |
| Phosphoric acid buffer | 25 mM |
| Ethylenediaminemonosuccinic acid | 0.2 g |
| Solution of metal salt mixture* | 0.5 ml |

*Solution of metal salt mixture (100 ml): sodium sulfate, 56 g; magnesium chloride hexahydrate, 8 g; calcium chloride, 0.8 g; manganese sulfate tetrahydrate, 0.6 g; ferric chloride hexahydrate, 0.12 g; zinc sulfate, 0.06 g.

(2) Production Reaction

A 20 ml portion was taken from each culture and placed in a centrifuging tube. Each culture in the tube was centrifuged at 10,000 rpm and 5° C. for 5 minutes, and the cells separated were washed twice with 50 mM phosphoric acid buffer having a pH of 7.5. The cells of each strain were then suspended in 5 ml of 50 mM phosphoric acid buffer with a pH of 7.5 containing 200 mM fumaric acid and 200 mM ethylenediamine. The reaction was conducted with shaking at 30° C. for 24 hours.

After completion of the reaction, the amount of the thus-produced ethylenediaminedisuccinic acid (EDDS) contained in the reaction mixture was determined by centrifuging the reaction mixture at 15,000 rpm and 5° C. for 5 minutes to remove the cells and analyzing the resulting supernatant by liquid chromatography (column, WAKOSIL 5C8 (Wako Pure Chemical Industries, Ltd., Japan); eluent, 50 mM phosphoric acid with a pH of 2 containing 10 mM tetra-n-butylammonium hydroxide and 0.4 mM $CuSO_4$). The optical purity of the reaction product was determined with an optical resolution column (MCI GEL; CRS 10W (Mitsubishi Chemical Industries Ltd., Japan)).

The reaction product was separated and purified by the technique described in T. Nishikiori et al., *J. Antibiotics*, 37, 426 (1984), in which an ion-exchange resin is used. The crystals obtained were analyzed by NMR spectrometry and mass spectrometry to ascertain the chemical structure of the reaction product.

(3) Results

| | Strain | |
|---|---|---|
| | Burkholderia sp. KK-5 | Burkholderia sp. KK-9 |
| Amount of EDDS produced (mM) | 40 | 53 |
| Optical characteristics | S,S | S,S |
| Optical purity (% ee) | 97 | 97 |

EXAMPLE 2

(1) Culture and Production Reaction

*Arthrobacter sp.* KK-3 was taken out from a slant broth agar medium in an amount of one platinum loop and inoculated into a 500-ml Erlenmeyer flask containing 100 ml of the culture medium shown in Example 1. The strain was cultured with shaking at 30° C. for 3 days. The cells of the strain were collected, washed, and subjected to a production reaction under the same conditions as in Example 1. The amount of the EDDS produced and the optical purity thereof were determined in the same manner as in Example 1.

(2) Results

| | Strain Arthrobacter sp. KK-3 |
|---|---|
| Amount of EDDS produced (mM) | 57 |
| Optical characteristics | S,S |
| Optical purity (% ee) | 97 |

EXAMPLE 3

(1) Culture and Production Reaction

*Paracoccus sp.* KK-6 was cultured, and the cells of the cultured strain were subjected to a production reaction, in the same manner as in Example 1. The amount of the EDDS produced and the optical purity thereof were determined in the same manner as in Example 1.

(2) Results

| | Strain Paracoccus sp. KK-6 |
|---|---|
| Amount of EDDS produced (mM) | 63 |
| Optical characteristics | S,S |
| Optical purity (% ee) | 72 |

EXAMPLE 4

(1) Culture and Production Reaction

*Burkholderia sp.* KK-5 was cultured, and the cells of the cultured strain were collected and subjected to production reactions in the same manner as in Example 1. In the production reactions, 200 mM 1,3-propanediamine, 200 mM 1,3-phenylenediamine, and 200 mM 1,4-phenylenediamine were each used in place of 200 mM ethylenediamine. The amount of each reaction product was determined by the same liquid chromatography as in Example 1 using a chemically synthesized product as a standard. The chemical structure of each reaction product was ascertained by NMR spectrometry after the reaction product was separated and purified by the technique proposed by T. Nishikiori et al. shown in Example 1.

(2) Results

| Diamine | Product | Amount (mM) |
| --- | --- | --- |
| 1,3-Propanediamine | 1,3-propanediamine-disuccinic acid | 43 |
| 1,3-Phenylenediamine | 1,3-phenylenediamine-disuccinic acid | 33 |
| 1,4-Phenylenediamine | 1,4-phenylenediamine-disuccinic acid | 61 |

EXAMPLE 5

(1) Culture and Production Reaction

*Paracoccus sp.* KK-6 was cultured, and the cells of the cultured strain were collected and subjected to production reactions, in the same manner as in Example 1. In the production reactions, 200 mM 1,3-phenylenediamine and 200 mM 1,4-phenylenediamine were each used in place of 200 nM ethylenediamine. The amount of each reaction product and the chemical structure thereof were determined or ascertained in the same manner as in Example 4.

(2) Results

| Diamine | Product | Amount (mM) |
| --- | --- | --- |
| 1,3-Phenylenediamine | 1,3-phenylenediamine-disuccinic acid | 25 |
| 1,4-Phenylenediamine | 1,4-phenylenediamine-disuccinic acid | 48 |

EXAMPLE 6

(1) Culture and Production Reaction

*Hafnia alvei* ATCC 9760 was cultured by the method described in *Meth. Enzymol.*, Vol. XIII, pp. 354–361 (1969) (1% yeast extract, 1% tripton, 0.5% dipotassium hydrogen phosphate; 48-hour static culture at 30° C). The cells of the cultured strain were collected and subjected to a production reaction, and the amount of the EDDS produced and the optical purity thereof were determined in the same manner as in Example 1.

(2) Results

|  | Strain *Hafnia alvei* ATCC 9760 |
| --- | --- |
| Amount of EDDS produced (mM) | 10 |
| Optical characteristics | R,S |
| Optical purity (% ee) | 99 |

EXAMPLE 7

(1) Production Reaction using Enzyme

A production reaction was carried out in the same manner as in Example 1, except that an L-aspartase manufactured by SIGMA Co, (L-aspartate ammonialysate; EC 4.3.1.1) derived from *Hafnia alvei* ATCC 9760 was used in a concentration of 5 mg per 5 ml of the reaction mixture.

(2) Results

|  | Enzyme L-Aspartate ammonialysate; EC 4.3.1.1 derived from *Hafnia alvei* ATCC 9760 |
| --- | --- |
| Amount of EDDS produced (mM) | 50 |
| Optical characteristics | R,S |
| Optical purity (% ee) | 99 |

EXAMPLE 8

(1) Culture and Production Reaction

*Acidovorax sp.* TN-51 was cultured, and the cells of the cultured strain were subjected to a production reaction in the same manner as in Example 1. The amount of the EDDS produced and the optical purity thereof were determined in the same manner as in Example 1.

(2) Results

|  | Strain *Acidovorax sp.* TN-51 |
| --- | --- |
| Amount of EDDS produced (mM) | 62 |
| Optical characteristics | S,S |
| Optical purity (% ee) | 98 |

EXAMPLE 9

(1) Culture and Production Reaction

*Acidovorax sp.* TN-51 was cultured and the cells of the cultured strain were subjected to production reactions in the same manner as in Example 4. The amount of each reaction product and the chemical structure thereof were determined in the same manner as in Example 4.

(2) Results

| Diamine | Product | Amount (mM) |
| --- | --- | --- |
| 1,3-Propanediamine | 1,3-propanediamine-disuccinic acid | 56 |
| 1,3-Phenylenediamine | 1,3-phenylenediamine-disuccinic acid | 41 |
| 1,4-Phenylenediamine | 1,4-phenylenediamine-disuccinic acid | 66 |

EXAMPLE 10

(1) Culture and Production Reaction

*Sphingomonas sp.* TN-28, *Brevundimonas sp.* TN-30 and *Pseudomonas sp.* TN-131 were cultured and the cells of each cultured strain were subjected to a production reaction, in the same manner as in Example 1. The amount of the EDDS produced and the optical purity thereof were determined in the same manner as in Example 1.

(2) Results

| | Strain | | |
|---|---|---|---|
| | Sphingomonas sp. TN-28 | Brevundimonas sp. TN-30 | Pseudomonas sp. TN-131 |
| Amount of EDDS produced (mM) | 61 | 55 | 68 |
| Optical characteristics | S,S | S,S | S,S |
| Optical purity (% ee) | 80 | 92 | 94 |

EXAMPLE 11

(1) Culture and Preparation of Crude Enzyme Solution

*Sphingomonas sp.* TN-28, *Brevundimonas sp.* TN-30 and *Pseudomonas sp.* TN-131 were cultured, and the cells of each cultured strain were collected and washed, in the same manner as Example 1. The cells of each strain were suspended in 1.5 ml of 50 mM phosphoric acid buffer having a pH of 7.5. This suspension was treated with ultrasonic for 30 minutes with cooling with ice to disrupt the cells. Each suspension was then centrifuged at 10,000 rpm for 30 minutes to obtain a supernatant.

(2) Production Reaction

A 0.5 ml portion of each supernatant was mixed with 1.5 ml of 50 mM phosphoric acid buffer with a pH of 7.5 containing 200 mM fumaric acid and 200 mM ethylenediamine. The reaction was conducted with shaking at 30° C. for 24 hours. The amount of the reaction product and the optical purity thereof were determined in the same manner as in Example 1.

(3) Results

| | Strain | | |
|---|---|---|---|
| | Sphingomonas sp. TN-28 | Brevundimonas sp. TN-30 | Pseudomonas sp. TN-131 |
| Amount of EDDS produced (mM) | 85 | 72 | 93 |
| Optical characteristics | S,S | S,S | S,S |
| Optical purity (% ee) | 96 | 98 | 98 |

EXAMPLE 12

(1) Culture and Production Reaction

*Burkholderia sp.* KK-5 and *Acidovorax sp.* TN-51 were cultured, and the cells of each cultured strain were collected and subjected to a production reaction, in the same manner as in Example 1. In the production reaction, 200 mM 1,3-cyclohexanediamine was used in place of 200 mM ethylenediamine. The amount of the 1,3-cyclohexanediamine-N,N'-disuccinic acid obtained as a reaction product was determined by liquid chromatography under the same conditions as in Example 1 using a chemically synthesized product as a standard. The chemical structure of the reaction product was ascertained by NMR spectrometry after the reaction product was separated and purified by the technique proposed by T. Nishikiori et al. shown in Example 1.

(2) Results

| | Strain | |
|---|---|---|
| | Burkholderia sp. KK-5 | Acidovorax sp. TN-51 |
| Amount of 1,3-cyclohexanediamine-N,N'-disuccinic acid (mM) | 26 | 21 |

EXAMPLE 13

*Escherichia coli* JM 109 (requiring thymine) was aerobically cultured at 37° C. for 3 days in an LB medium (1% tripton, 1% yeast extract, 0.5% common salt) containing 0.2% ethylenediamine-N,N'-disuccinic acid. The cells of the cultured strain were collected, washed and subjected to a production reaction, and the amount of the reaction product was determined in the same manner as in Example 1.

(2) Results

| | Strain *Escherichia coli* JM 109 |
|---|---|
| Amount of EDDS produced (mM) | 7 |
| Optical characteristics | R,S |
| Optical purity (% ee) | 95 |

According to the present invention, a method of industrially producing an optically active amino acid by the action of a microorganism is provided in which the amino acid is produced from inexpensive materials, i.e., fumaric acid and an amino compound, under mild conditions of ordinary temperature and ordinary pressure.

While the invention has been described in detail and with reference to specific embodiments thereof, it will be apparent to one skilled in the art that various changes and modifications can be made therein without departing from the spirit and scope thereof.

What is claimed is:

1. A method of producing an optically active amino acid of formula (III):

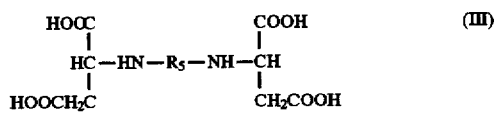

which comprises:
treating a mixture of fumaric acid and an amino group-containing compound of formula (IV):

wherein $R_5$ is an alkylene group, a cycloalkylene group or a phenylene group with a microorganism or treated cells thereof having a lyase activity which is able to convert a mixture of fumaric acid and the compound of formula (IV) into the optically active amino acid of formula (III), producing the compound of formula (III), and isolating the optically active amino acid of formula (III).

2. The method as claimed in claim 1, wherein $R_5$ is an alkylene group.

3. The method as claimed in claim 1, wherein said amino group-containing compound of formula (IV) is an alylenediamine having from 1 to 6 carbon atoms, and said optically active amino acid of formula (III) is the corresponding S,S- or R,S-diaminoalkylene-N,N'-disuccinic acid thereof.

4. The method as claimed in claim 3, wherein said alkylenediamine having from 1 to 6 carbon atoms is ethylenediamine, and said optically active amino acid is S,S-ethylenediamine-disuccinic acid.

5. The method as claimed in claim 1, wherein said amino compound of formula (IV) is a phenylene-diamine, and said optically active amino acid of formula (III) is the corresponding phenylenediamine-N,N'-disuccinic acid thereof.

6. The method as claimed in claim 1, wherein said amino compound of formula (IV) is cyclohexylenediamine, and said optically active amino acid of formula (III) is the corresponding cyclohexylenediamine-N,N'-disuccinic acid thereof.

7. The method as claimed in any one of claims 1 to 6 wherein said microorganism belongs to the genus selected from the group consisting of Burkholderia, Arthrobacter, Paracoccus and Hafnia.

8. The method as claimed in claim 7, wherein said microorganism is *Burkholderia sp.* KK-5 or *Burkholderia sp.* KK-9 or *Arthrobacter sp.* KK-3 or *Paracoccus sp.* KK-6 or *Hafnia alvei* ATCC 9760.

9. The method as claimed in any one of claims 1 to 6 wherein said microorganism belongs to the genus selected from the group consisting of Acidovorax, Sphingomonas, Brevundimonas and Pseudomonas.

10. The method as claimed in claim 9, wherein said microorganism is *Acidovorax sp.* TN-51 or *Brevundimonas sp.* TN-30 or *Pseudomonas sp.* TN-131 or *Sphingomonas sp.* TN-28.

11. The method as claimed in any one of claims 1 to 6, wherein said microorganism belongs to the genus Escherichia.

12. The method as claimed in claim 11, wherein said microorganism is *Escherichia coli* JM 109.

* * * * *